(12) United States Patent
Egi et al.

(10) Patent No.: US 6,284,758 B1
(45) Date of Patent: Sep. 4, 2001

(54) ANGIOGENESIS PROMOTERS AND ANGIOGENESIS POTENTIATORS

(75) Inventors: Yasuhiro Egi, Hirakata; Hideaki Kido, Fukuoka; Kazutaka Hayashi; Yoshiji Kubo, both of Hirakata; Norifumi Nakamura, Osaka, all of (JP)

(73) Assignees: Welfide Corporation, Osaka; Nissan Chemical Industries, Ltd., Tokyo, both of (JP)

( * ) Notice: Subject to any disclaimer, the term of this patent is extended or adjusted under 35 U.S.C. 154(b) by 0 days.

(21) Appl. No.: 09/486,327
(22) PCT Filed: Aug. 26, 1998
(86) PCT No.: PCT/JP98/03820
 § 371 Date: Feb. 25, 2000
 § 102(e) Date: Feb. 25, 2000
(87) PCT Pub. No.: WO99/11268
 PCT Pub. Date: Mar. 11, 1999

(30) Foreign Application Priority Data

Aug. 28, 1997 (JP) .................................................. 9-232644

(51) Int. Cl.$^7$ .......................... A61K 31/50; C07D 401/12
(52) U.S. Cl. ...................................... 514/252.03; 544/238
(58) Field of Search ........................ 544/238; 514/252.03

(56) References Cited

U.S. PATENT DOCUMENTS 5,654,277 * 8/1997 Eyal et al. .............................. 514/18

FOREIGN PATENT DOCUMENTS 7-252237 10/1995 (JP) .
7-285869 10/1995 (JP) .
91/16314 10/1991 (WO) .

OTHER PUBLICATIONS

Atz et al. Nitric Oxide Inhalation, Endothelial Cell Res, pt B, 471–503, Jan. 1999.*
Asif Ahmed et al., Lab. Invest., (1997), 76(6), pp. 779–791.

* cited by examiner

Primary Examiner—Richard L. Raymond
Assistant Examiner—Hong Liu
(74) Attorney, Agent, or Firm—Wenderoth, Lind & Ponack, L.L.P.

(57) ABSTRACT

An angiogenesis promoter and angiogenesis potentiator containing a pyridazinone compound of the formula (I)

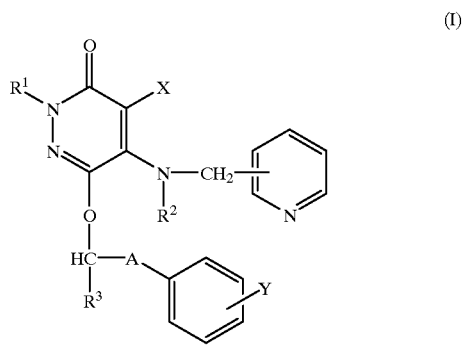

wherein each symbol is as defined in the specification, or a pharmacologically acceptable salt thereof, as an active ingredient. The pyridazinone compound (I) and a pharmacologically acceptable salt thereof in the present invention promote angiogenesis and potentiate the angiogenic effect of a drug having such effect, and are useful as an angiogenesis promoter and angiogenesis potentiator.

8 Claims, 6 Drawing Sheets

*:p<0.05, **:p<0.01 relative to control ized by methylene, ethylene, propylene, butylene, pentylene, hydroxymethylene, 1-hydroxyethylene, 2-hydroxyethylene, 3-hydroxypropylene and the like.

ANGIOGENESIS PROMOTERS AND ANGIOGENESIS POTENTIATORS

TECHNICAL FIELD

The present invention relates to angiogenesis promoters and angiogenesis potentiators, which contain, as an active ingredient, a specific pyridazinone compound or a pharmacologically acceptable salt thereof.

BACKGROUND ART

The below-noted specific pyridazinone compound in the present invention is known to have superior platelet aggregation inhibitory effect, cardiotonic effect, vasodilating effect, anti-SRS-A (Slow Reacting Substances of Anaphylaxis) effect, thromboxane $A_2$ synthase inhibitory effect and the like (JP-B-7-107055, JP-A-7-285869), and is a drug expected to be an antiplatelet agent and the like.

However, there has not been any report on the effect of the pyridazinone compound on angiogenesis.

DISCLOSURE OF THE INVENTION

The present inventors have conducted various studies of the effect of the pyridazinone compound on the angiogenesis and found that the pyridazinone compound promotes angiogenesis and potentiates an angiogenic effect of a drug having such effect, which resulted in the completion of the present invention.

Accordingly, the present invention provides the following.

An angiogenesis promoter containing a pyridazinone compound of the formula (I)

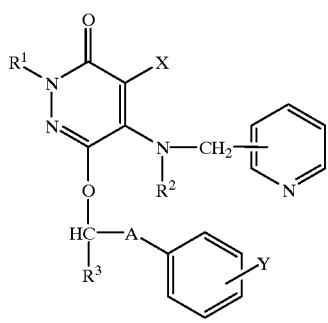

(I)

wherein $R^1$, $R^2$ and $R^3$ are each independently a hydrogen atom or a lower alkyl, X is a halogen atom, cyano or a hydrogen atom, Y is a halogen atom, trifluoromethyl or a hydrogen atom, and A is $C_1$–$C_8$ alkylene optionally substituted by hydroxyl group, or a pharmacologically acceptable salt thereof (hereinafter to be referred to as pyridazinone compounds) as an active ingredient.

A method of promoting angiogenesis, which comprises administering a pyridazinone compound.

Use of a pyridazinone compound for the production of an angiogenesis promoter.

A pharmaceutical composition for promoting angiogenesis, which comprises a pyridazinone compound and a pharmaceutically acceptable carrier.

A commercial package comprising the above-mentioned pharmaceutical composition, and a written matter associated therewith, the written matter stating that the pharmaceutical composition can or should be used for promoting angiogenesis.

A potentiator of a drug having an angiogenic effect, which contains a pyridazinone compound as an active ingredient.

A method of potentiating an angiogenic effect of a drug having such effect, which comprises administering a pyridazinone compound.

Use of a pyridazinone compound for the production of a potentiator of a drug having an angiogenic effect.

A pharmaceutical composition for potentiating an angiogenic effect of a drug having such effect, which contains a pyridazinone compound and a pharmaceutically acceptable carrier.

A commercial package comprising the above-mentioned pharmaceutical composition, and a written matter associated therewith, the written matter stating that the pharmaceutical composition can or should be used for potentiating an angiogenic effect of a drug having such effect.

The pyridazinone compound in the present invention is preferably a compound of the formula (I), wherein $R^1$ and $R^2$ are each hydrogen atom, $R^3$ is hydrogen atom or alkyl having 1 to 4 carbon atoms, X is halogen atom, Y is halogen atom or hydrogen atom and A is $C_1$–$C_5$ alkylene optionally substituted by hydroxyl group.

Particularly preferable pyridazinone compound of the formula (I) (hereinafter to be referred to as pyridazinone compound (I)) is, for example, 4-bromo-6-[3-(4-chlorophenyl)-propoxy]-5-(3-pyridylmethylamino)-3-(2H)-pyridazinone.

Angiogenesis means that endothelial cells bud from an existing blood vessel and form a new blood vessel. The process of the formation is complicated and is an important phenomenon observed in various aspects in the living body, such as angiogenesis for development and growth, pathologic angiogenesis (e.g. growth of tumor, diabetic retinopathy) and the like.

Administration of an angiogenesis promoter to the patients with cancer or diabetic retinopathy is prohibited because it promotes pathologic angiogenesis.

However, an angiogenesis promoter is useful in that it complements and potentiates the efficacy of a pharmaceutical agent that directly acts on the mainly diseased artery (artery mainly causing the disease), because it forms a collateral circulatory path irrespective of the mainly diseased artery.

The symbols used in this specification are explained in the following.

The lower alkyl at $R^1$, $R^2$ and $R^3$ has 1 to 6 carbon atoms and may be linear or branched. Examples thereof include methyl, ethyl, n-propyl, isopropyl, n-butyl, isobutyl, sec-butyl, t-butyl, pentyl, hexyl and the like.

$R^1$ and $R^2$ are each preferably a hydrogen atom and $R^3$ is preferably a hydrogen atom or alkyl having 1 to 4 carbon atoms.

The alkyl having 1 to 4 carbon atoms at $R^3$ is exemplified by methyl, ethyl, n-propyl, isopropyl, n-butyl, isobutyl, sec-butyl, t-butyl and the like.

The halogen atom at X and Y means fluorine atom, chlorine atom, bromine atom or iodine atom.

Preferable X is a halogen atom and preferable Y is a halogen atom and a hydrogen atom.

The $C_1$–$C_8$ alkylene optionally substituted by hydroxyl group at A may be linear or branched and is exemplified by methylene, ethylene, propylene, butylene, pentylene, hexylene, heptylene, octylene, 2,2-dimethylethylene, 2,2-diethylethylene, 2,2-di-n-propylethylene, hydroxymethylene, 1-hydroxyethylene, 2-hydroxyethylene, 3-hydroxypropylene and the like.

Preferable A is $C_1$–$C_5$ alkylene optionally substituted by hydroxyl group.

In the formula (I), methylene group and pyridine ring may be bonded at any position, but preferably bonded at the 3-position relative to the nitrogen atom of the pyridine ring.

Y may be substituted at any position on the benzene ring, but preferably at the 4-position.

Particularly, the pyridazinone compound of the formula (I) wherein $R^1$ and $R^2$ are hydrogen atoms, $R^3$ is hydrogen atom or alkyl having 1 to 4 carbon atoms, X is halogen atom, Y is halogen atom or hydrogen atom and A is $C_1$–$C_5$ alkylene optionally substituted by hydroxyl group is preferable.

More preferable pyridazinone compounds (I) include 4-bromo-6-(3-phenylpropoxy)-5-(3-pyridylmethylamino)-3(2H)-pyridazinone, 4-chloro-6-(3-phenylpropoxy)-5-(3-pyridylmethylamino)-3(2H)-pyridazinone, 4-chloro-6-[3-(4-chlorophenyl)propoxy]-5-(3-pyridylmethylamino)-3(2H)-pyridazinone, 4-bromo-6-[3-(4-chlorophenyl)propoxy]-5-(3-pyridylmethylamino)-3(2H)-pyridazinone, 4-bromo-6-(2,2-dimethyl-3-phenylpropoxy)-5-(3-pyridylmethylamino)-3(2H)-pyridazinone, 4-chloro-6-(2,2-dimethyl-3-phenylpropoxy)-5-(3-pyridylmethylamino)-3(2H)-pyridazinone, 4-bromo-6-[3-(4-chlorophenyl)-2,2-dimethylpropoxy]-5-(3-pyridylmethylamino)-3(2H)-pyridazinone, 4-chloro-6-[3-(4-chlorophenyl)-2,2-dimethylpropoxy]-5-(3-pyridylmethylamino)-3(2H)-pyridazinone, 4-bromo-6-[3-(4-chlorophenyl)-3-hydroxypropoxy]-5-(3-pyridylmethylamino)-3(2H)-pyridazinone, 4-chloro-6-[3-(4-chlorophenyl)-3-hydroxypropoxy]-5-(3-pyridylmethylamino)-3(2H)-pyridazinone, 4-bromo-6-[3-(4-chlorophenyl)-2-hydroxypropoxy]-5-(3-pyridylmethylamino)-3(2H)-pyridazinone and 4-chloro-6-[3-(4-chlorophenyl)-2-hydroxypropoxy]-5-(3-pyridylmethylamino)-3(2H)-pyridazinone.

The pyridazinone compound (I) in the present invention encompasses stereoisomers and optical isomers.

The pyridazinone compound (I) can be produced by a method disclosed in, for example, JP-B-7-107055, U.S. Pat. No. 5,314,883, EP-A-482208, JP-A-7-252237, U.S. Pat. No. 5,750,523 and EP-A-742211.

The pharmacologically acceptable salts of pyridazinone compound (I) include salts with inorganic acid (e.g., hydrochloride, hydrobromide, phosphate, sulfate and the like), salts with organic acid (e.g., acetate, succinate, maleate, fumarate, malate, tartrate and the like), and the like.

The pyridazinone compound (I) can be converted to the above-mentioned salts by known methods.

The pyridazinone compound (I) and pharmacologically acceptable salts thereof can be used as an angiogenesis promoter by themselves. They may be also used as a potentiator of the angiogenic effect of a drug having such effect by concurrently using the drug.

The drug having an angiogenic effect may be a growth factor such as a basic fibroblast growth factor;b-FGF, an endothelial cell growth factor;ECGF, an epidermal growth factor;EGF, a transforming growth factor-β;TGF-β, a platelet-derived endothelial cell growth factor;PDGF, a vascular endothelial growth factor;VEGF, a vascular permeability factor;VPF and the like, heparin, adenosine and the like.

The pyridazinone compound (I) and pharmacologically acceptable salts thereof are superior as a potentiator of the angiogenic effect of a growth factor, particularly b-FGF.

The effects of the present invention can be confirmed by any known method which is free of limitation.

The pyridazinone compound (I) and pharmacologically acceptable salts thereof, which are the active ingredients in the present invention, are extremely low toxic and show an angiogenesis-promoting effect and potentiation of the angiogenic effect of a drug in mammals such as human, dog, cow, horse, rabbit, mouse, rat and the like.

The pyridazinone compound (I) and pharmacologically acceptable salts thereof can be administered parenterally in the form of injection (subcutaneous, intravenous, intramuscular, intraperitoneal injections), ointment, suppository, aerosol agent and the like, or orally in the form of tablet, capsule, granule, pill, syrup, liquid, emulsion, suspension and the like.

The pyridazinone compound (I) and salts thereof can be formulated into a preparation for administration, according to conventional methods of drug production.

The tablet, capsule, granule and pill for oral administration can be prepared using excipienl (e.g., sucrose, lactose, glucose, starch, mannitol and the like), binder (e.g., syrup, acacia, gelatin, sorbitol, tragacanth, methylcellulose, polyvinylpyrrolidone and the like), disintegrant (e.g., starch, carboxymethylcellulose or calcium salt thereof, microcrystalline cellulose, polyethylene glycol and the like), lubricant (e.g., talc, magnesium stearate, calcium stearate, silica and the like), glidant (e.g., sodium lauryl sulfate, glycerol and the like), and the like.

The injection, aerosol agent, syrup, liquid, emulsion and suspension can be prepared using a solvent for the active ingredient (e.g., water, ethyl alcohol, isopropyl alcohol, propylene glycol, 1,3-butylene glycol, polyethylene glycol and the like), a surfactant (e.g., sorbitan fatty acid ester, polyoxyethylenesorbitan fatty acid ester, polyoxyethylene fatty acid ester, polyoxyethylene ether of hydrogenated caster oil, lecithin and the like), a suspending agent (e.g., cellulose derivatives such as carboxymethylcellulose sodium salt, methylcellulose and the like, natural gums such as tragacanth, acacia and the like), a preservative (e.g., p-hydroxybenzoate, benzalkonium chloride, sorbate and the like), and the like. A suppository can be prepared using, for example, polyethylene glycol, lanolin, coconut oil and the like.

The dose of the pyridazinone compound (I) and a salt thereof can be determined as appropriate according to the age, body weight, disease state and the like of the patient. It is generally 0.001 mg–5 g/day, preferably 0.005–1000 mg/day, for an adult (human), which is administered in one to several doses a day.

When the pyridazinone compound (I) or a pharmacologically acceptable salt thereof is used as a potentiator of the angiogenic effect of a drug having such effect, the pyridazinone compound in the present invention and the drug having an angiogenic effect are administered in such a manner that they are both present in the body during the same period of time. The use and dose of the drug having an angiogenic effect are free of limitation as long as they fall within the known ranges. They may be prepared into a single pharmaceutical preparation or separately into individual preparations. When they are separate preparations, the administration route and dose may be the same or different.

EXAMPLES

Figure 1:
FIG. 1 is a photograph showing the neovascularized blood vessel at day 7 of the test in a rat sponge model group administered with a vehicle.

The present invention is explained in detail in the following Examples and Experimental Examples. The invention is not limited by these Examples in any way.

Experimental Example 1

Promotion of Angiogenesis by Compound A

Method:

Rats were anesthetized by intraperitoneal administration of sodium pentobarbital (50 mg/kg), and the dorsal median line was incised for about 1 cm and an air pocket was made subcutaneously at about 2.5 cm toward the tail side with a Kocher clamp. A hemostatic gelatin sponge (Spongel®, 10 mm×10 mm×7 mm; manufactured by Yamanouchi Pharmaceutical Co., Ltd.) impregnated with physiological saline was embedded therein. The opening was sutured and antisepticized to give a test animal model.

As a reagent, compound A (4-bromo-6-[3-(4-chlorophenyl)-propoxy]-5-(3-pyridylmethylamino)-3-(2H)-pyridazinone hydrochloride, 100 mg) produced by a conventional method was suspended in 0.5% methylcellulose solution (100 ml) in a mortar and used.

As a control, a vehicle (0.5% methylcellulose solution) was used. The vehicle was obtained by dissolving methylcellulose (5 g, manufactured by Kishida Chemical Industries, Ltd.) in distilled water (1000 ml).

The reagent (compound A) and the vehicle were orally administered repeatedly from the day of sponge embedding at a dose of 10 ml/kg once a day for 4 days or 7 days. The administration was performed 30 minutes before anesthetizing the animal on the very day of embedding, and the sponge was removed on the next day of the final administration.

After 4 days or 7 days from the embedding, an excess amount of pentobarbital was intravenously injected to the animals for euthanasia. The back was opened, and the tissue surrounding the embedded sponge was removed and the surface of the sponge was photographed. The sponge was taken out and placed in a 0.1M aqueous ammonia (2 ml), which was stood for 4 hr to extract hemoglobin in the sponge. The extract (100 µl) was taken, and hemoglobin was quantitated using an assay kit (hemoglobin B-TESTWAKO; manufactured by Wako Pure Chemical Industries, Ltd.) and used as the index of angiogenesis. The amount of hemoglobin in the sponge was calculated by the following formula.

Amount of hemoglobin in sponge (mg/sponge)=hemoglobin (mg) in extract (100 µl)×20 (total extract 2 ml)

The obtained data were expressed in mean±standard error. For the evaluation of the angiogenic effect, an unpaired t-test was performed using the animals administered with the drug for 4 days or 7 days and respective vehicle groups as control to examine significant difference. The significance was ascribed at less than 5% risk rate.

Results:

1. Observation of Photograph

Figure 2:
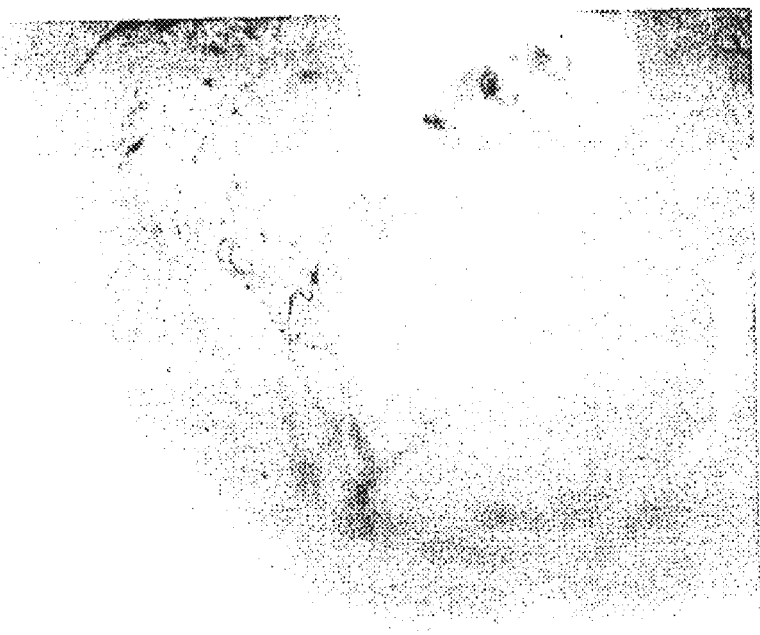
FIG. 2 is a photograph showing the neovascularized blood vessels at day 7 of the test in a rat sponge model group administered with compound A.

Both the reagent (compound A) administration group and vehicle administration group showed an increase of neovascularized blood vessels on the sponge surface at day 4 and day 7 of the test in proportion to the number of days lapsed from the initiation of the test. At day 7 of the test, the reagent (compound A) administration group (FIG. 2) showed more neovascularized blood vessels than in the vehicle administration group (FIG. 1).

2. Amount of Hemoglobin in Sponge

Figure 3:
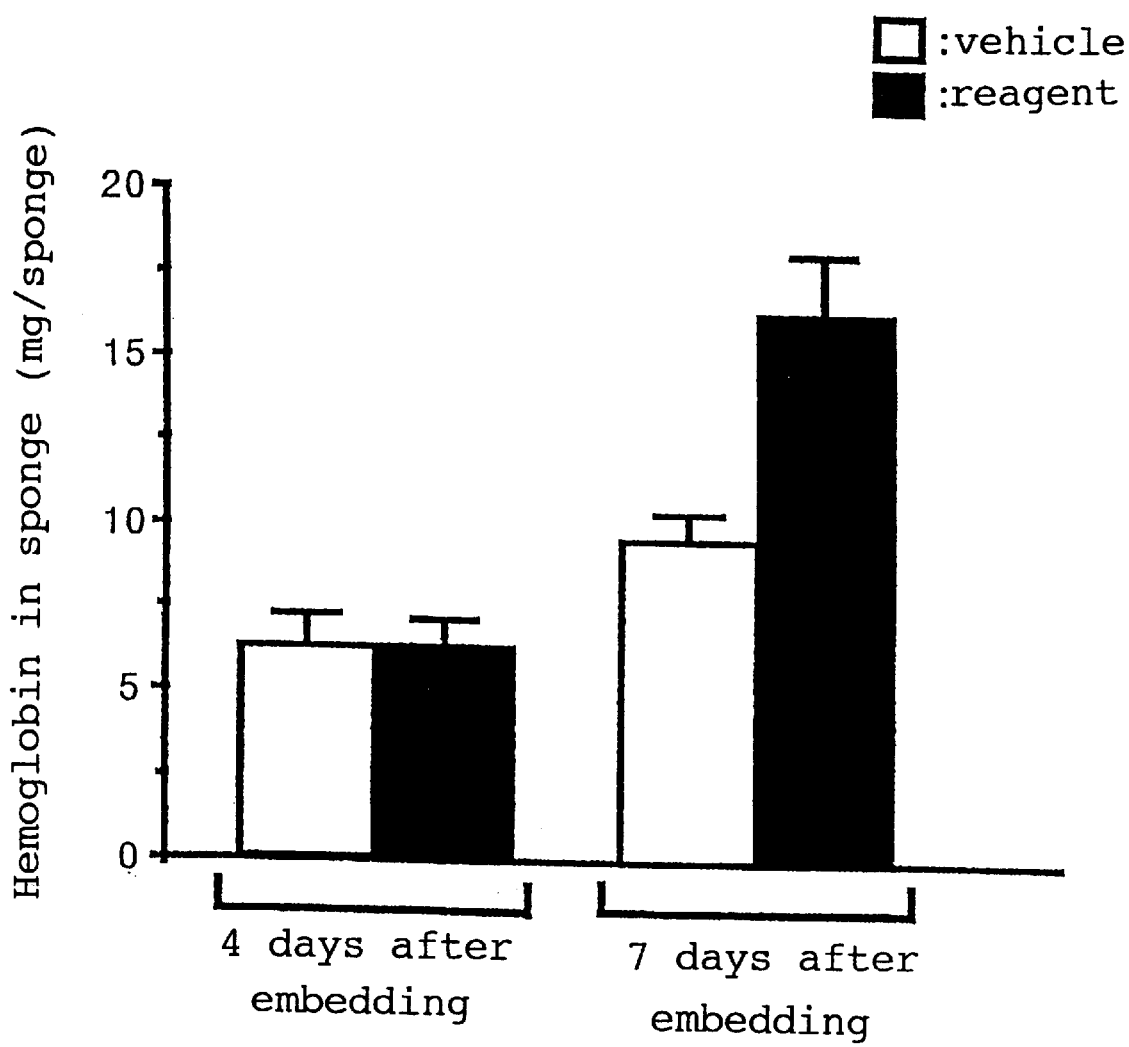
FIG. 3 shows the amount of hemoglobin in sponge in a rat sponge model, indicating the angiogenesis-promoting effect of compound A.

The results are shown in Table 1 and FIG. 3. Both the reagent (compound A) administration group and vehicle administration group showed an increase in the amount of hemoglobin in sponge at day 4 and day 7 of the test, in proportion to the number of days lapsed from the initiation of the test. At day 7 of the test, the reagent (compound A) administration group showed a significant increase as compared to the vehicle administration group.

TABLE 1

| | Hemoglobin in sponge (mg/sponge) | |
|---|---|---|
| Drug | 4 days after embedding | 7 days after embedding |
| Vehicle | 6.216 ± 0.903 (9) | 9.585 ± 0.774 (10) |
| Reagent (compound A) | 6.255 ± 0.807 (10) | 16.351 ± 1.836 ** (9) |

( ): number of animals
**: $p < 0.01$ relative to vehicle administration group, unpaired t-test

Experimental Example 2

Potentiation of Angiogenic Effect of b-FGF by Compound A

Method:

The test animal models were prepared in the same manner as in Experimental Example 1.

As a reagent, compound A (4-bromo-6-[3-(4-chlorophenyl)-propoxy]-5-(3-pyridylmethylamino)-3-(2H)-pyridazinone hydrochloride, 50 mg) produced by a conventional method was suspended in 0.5% methylcellulose solution (100 ml) in a mortar and used.

The vehicle (0.5% methylcellulose solution) was obtained by dissolving methylcellulose (5 g, manufactured by Kishida Chemical Industries, Ltd.) in distilled water (1000 ml).

A 0.1% bovine serum albumin (BSA)-physiological saline solution was prepared by dissolving BSA (0.1 g, Sigma) in physiological saline (100 Ml).

A b-FGF solution was prepared by dissolving recombinant b-FGF (20 µg, manufactured by BTI) in 0.1% BSA-physiological saline solution (2 ml).

A hemostatic gelatin sponge was the same as that used in Experimental Example 1.

The test group was divided into 3 groups. A sponge wetted with 100 µl of 0.1% BSA-physiological saline solution was embedded in group 1. A sponge (1 µg b-FGF/sponge) wetted with b-FGF solution (100 µl) was embedded in group 2 and group 3.

The vehicle was orally administered to group 1 and group 2, and the reagent (compound A) was orally administered to group 3 repeatedly from the day of sponge embedding at the dose of 10 ml/kg twice a day for 4 days.

In every test group, the administration began from the evening (single administration) of the very day of embedding. The time of administration of the drug was around 9 a.m. for the first administration and around 7 p.m. for the second administration. In consideration of the effect of the drug, the drug was not administered on the very day of sponge removal (7 times of administration in total).

After 4 days from the embedding, an excess amount of pentobarbital was intravenously injected to the animals for euthanasia. The back was opened, and the tissue surrounding the embedded sponge was removed and the surface of the sponge was photographed. The sponge was taken out and hemoglobin in the sponge was calculated in the same manner as in Experimental Example 1.

The obtained data were expressed in mean±standard error. For the evaluation of the angiogenic effect, a multiple comparison test by Tukey method was performed to examine significant difference. The significance was ascribed at less than 5% risk rate.

Results:

1. Observation of Photograph

Figure 4:
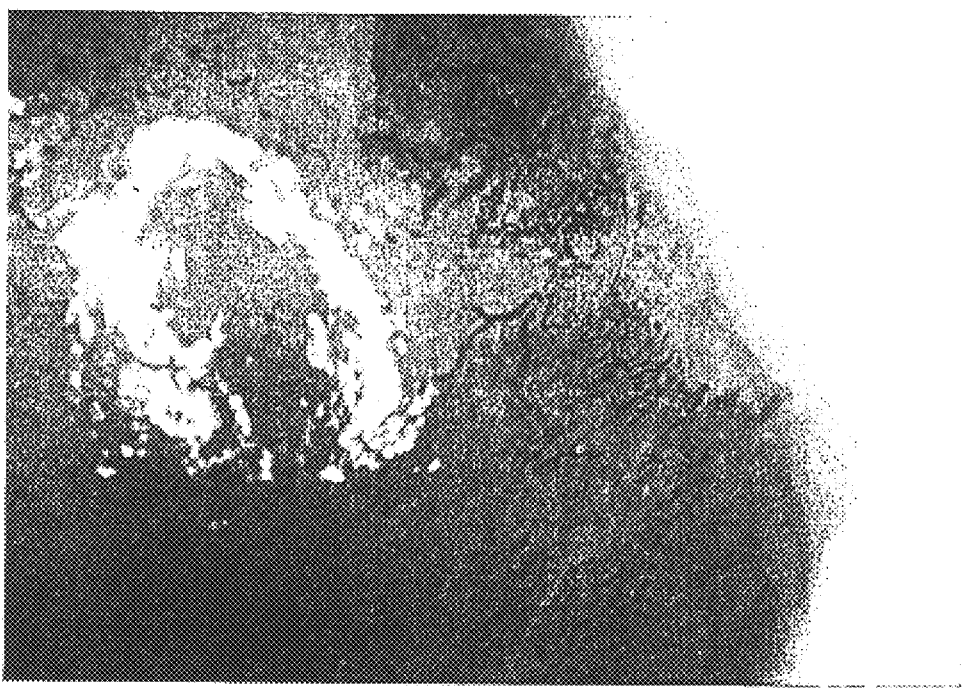
FIG. 4 is a photograph showing the neovascularized blood vessels at day 4 of the test in a rat sponge model group 1 administered with a BSA-physiological saline solution.
Figure 5:
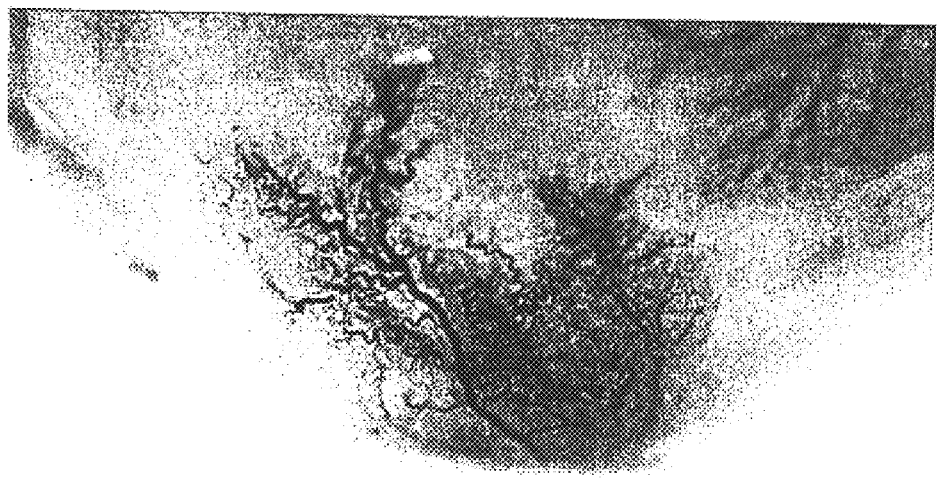
FIG. 5 is a photograph showing the neovascularized blood vessels at day 4 of the test in a rat sponge model group 2 administered solely with a basic fibroblast growth factor (b-FGF).
Figure 6:
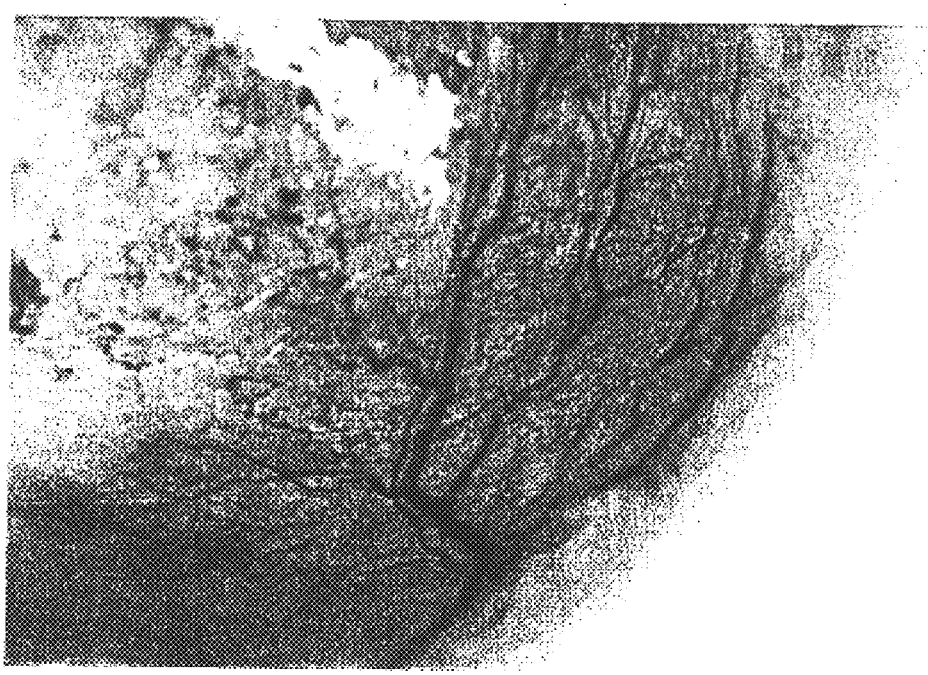
FIG. 6 is a photograph showing the neovascularized blood vessels at day 4 of the test in a rat sponge model group 3 co-administered with b-FGF and compound A.

The results are shown in FIG. 4, FIG. 5 and FIG. 6. At day 4 of the test, group 2 (b-FGF single administration group) visually showed more neovascularized blood vessels than in group 1 (0.1% BSA-physiological saline solution group), and group 3 (b-FGF and reagent (compound A, 5 mg/kg) co-administration group) showed still more neovascularized blood vessels than in group 2.

2. Amount of Hemoglobin in Sponge

Figure 7:
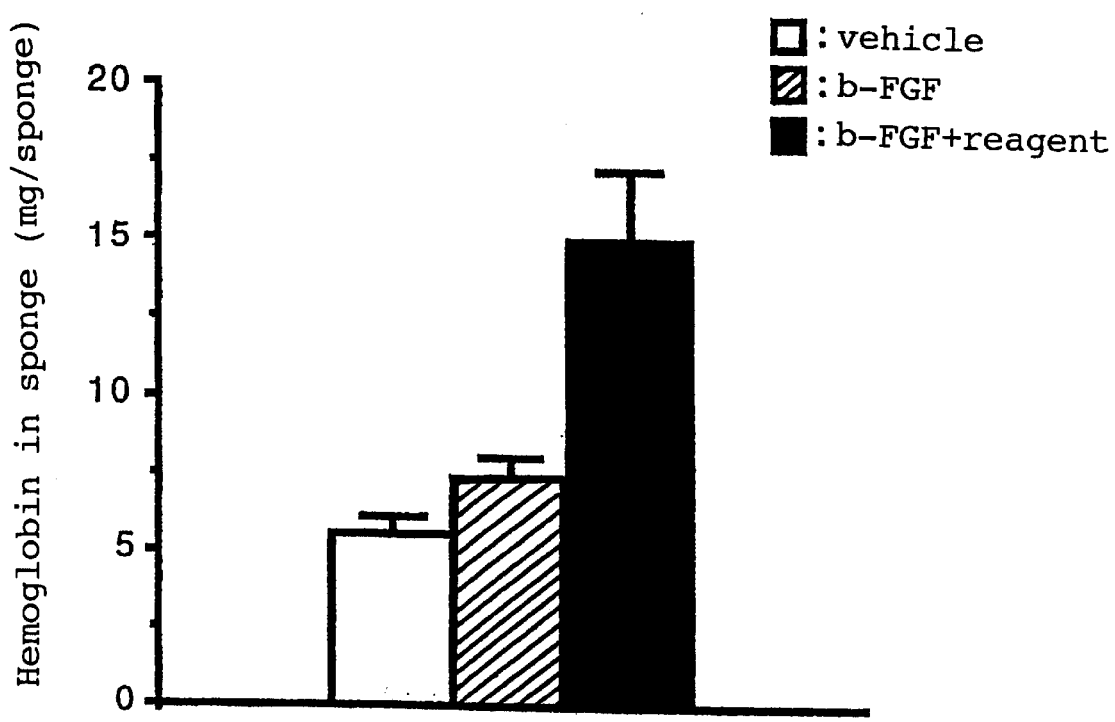
FIG. 7 shows the amount of hemoglobin in sponge in a rat sponge model, indicating angiogenic potency of b-FGF by compound A.

The results are shown in Table 2 and FIG. 7. The group 3 (b-FGF and reagent (compound A, 5 mg/kg) co-administration group) showed a significant increase in hemoglobin content as compared to group 1 (0.1% BSA-physiological saline solution group) and group 2 (b-FGF single administration group).

TABLE 2

| Test group | Oral administration | In-sponge administration | Hemoglobin in sponge (mg/sponge) at 4 days after embedding |
|---|---|---|---|
| Group 1 | Vehicle | BSA-physiological saline | 5.503 ± 0.562 (10) |
| Group 2 | Vehicle | b-FGF | 7.285 ± 0.715 (10) |
| Group 3 | Reagent (compound A) | b-FGF | 14.995 ± 2.307 ++,** (10) |

( ): number of animals,
++:p < 0.01 relative to group 1,
**:p < 0.01 relative to group 2 (Tukey method)

Experimental Example 3

Relationship Between Dose and Angiogenesis Promotion by Compound A

Method:

The test animal models were prepared in the same manner as in Experimental Example 1.

As a reagent, compound A (4-bromo-6-[3-(4-chlorophenyl)-propoxy]-5-(3-pyridylmethylamino)-3-(2H)-pyridazinone hydrochloride, 35 mg) produced by a conventional method was suspended in 0.5% methylcellulose solution (70 ml) in a mortar and used as a 5 mg/kg administration reagent.

This suspension was diluted two-fold and 5-fold with a vehicle (0.5% methylcellulose solution) to give 2.5 mg/kg administration reagent and 1 mg/kg administration reagent (respective dose 10 ml/kg). The vehicle (0.5% methylcellulose solution) was used as a control. The vehicle was obtained by dissolving methylcellulose (5 g, manufactured by Kishida Chemical Industries, Ltd.) in distilled water (1000 ml).

Each reagent (compound A) and the vehicle were orally administered repeatedly (7 times in total) from the day of sponge embedding at a dose of 10 ml/kg twice a day for 4 days. The sponge was removed on the next day of the final administration, and hemoglobin in the sponge was calculated in the same manner as Experimental in Example 1.

Each group contained 814 9 animals and the obtained data were expressed in mean±standard error. For the evaluation of the angiogenic effect, a Dunnett test was performed using the vehicle administration group as a control to examine significant difference. The significance was ascribed at less than 5% risk rate.

Figure 8:
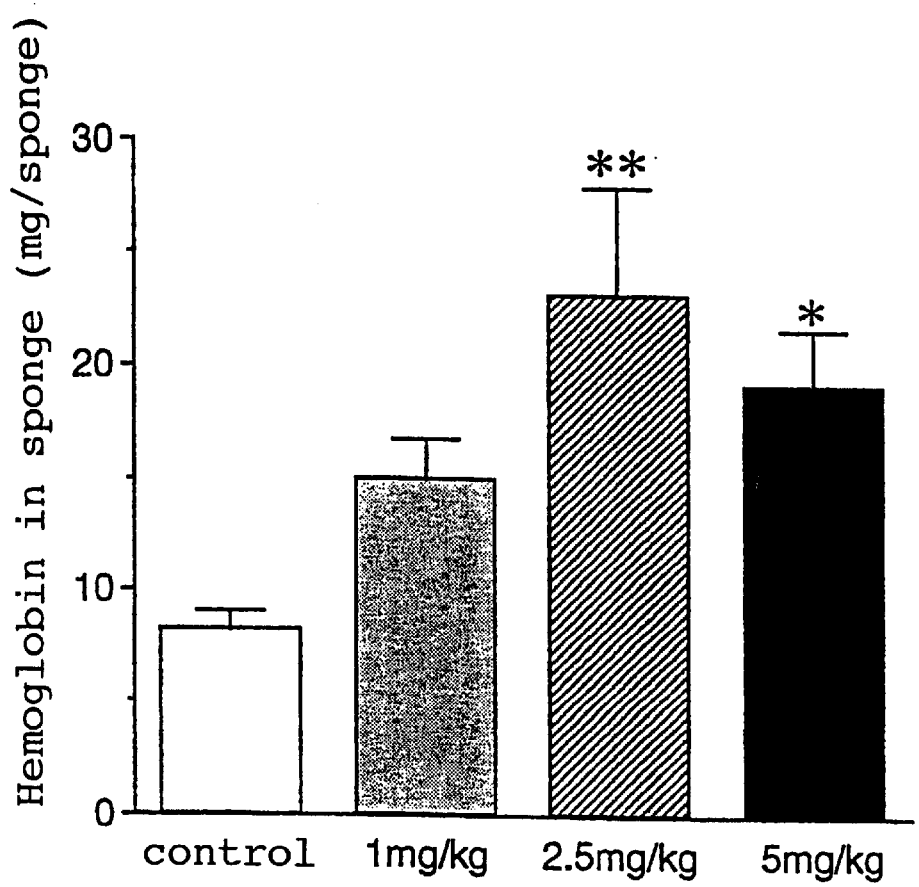
FIG. 8 shows the relationship between the dose and angiogenic efficacy by compound A in a rat sponge model.

Results:

The results are shown in FIG. 8. As compared to the vehicle administration group, 2.5 mg/kg administration group and 5 mg/kg administration group showed a significant increase in hemoglobin amount.

In the 5 mg/kg administration group, the effect tended to weaken somewhat, though a significant difference was found. This is postulated to be attributable to a decrease in blood flow due to hypotensive action, since the dose (5 mg/kg) of compound A causes hypotensive action in rat, based on vasodilating action.

This has clarified that compound A shows superior angiogenesis promotion effect at a dose substantially free from hypotensive action.

Experimental Example 4

Toxicity

The acute toxicity ($LD_{50}$) of compound A was not less than 2 g/kg by the oral administration to rat and dog, and the compound was found to be extremely low toxic.

From the above test results, it is evident that the pyridazinone compound (I) and a salt thereof show superior angiogenesis-promoting effect and potentiation of the angiogenic effect of a drug having such effect, and are low toxic.

Example 1 (tablet)

The following ingredients were mixed by a conventional method and prepared into sugar-coated tablets containing 50 mg of the active ingredient per tablet.

| | |
|---|---|
| Compound A | 10 g |
| lactose | 20 g |
| starch | 5 g |
| magnesium stearate | 0.1 g |
| calcium carboxymethylcellulose | 7 g |
| total | 42.1 g |

Example 2 (capsule)

The following ingredients were mixed by a conventional method and filled in gelatin capsules to give capsules containing 50 mg of the active ingredient per capsule.

| | |
|---|---|
| Compound A | 10 g |
| lactose | 20 g |

-continued

| | |
|---|---|
| microcrystalline cellulose | 10 g |
| magnesium stearate | 1 g |
| total | 41 g |

Example 3 (ointment)

The following ingredients were mixed by a conventional method to give a 1 wt% ointment.

| | |
|---|---|
| Compound A | 1 g |
| olive oil | 20 g |
| white petrolatum | 79 g |
| total | 100 g |

Example 4 (aerosol suspension)

The following ingredients (A) were mixed and the obtained mixed solution was charged in a container equipped with a valve. A propellant (B) was pressed therein from a valve nozzle at 20° C. to about 2.46–2.81 mg/cm² gauge pressure to give an aerosol suspension.

| | |
|---|---|
| (A)Compound A | 0.25 wt % |
| isopropyl myristate | 0.10 wt % |
| ethanol | 26.40 wt % |
| (B)1,2-dichlorotetrafluoroethane and 1-chloropentafluoroethane (60–40 wt %) | 73.25 wt % |

Industrial Applicability

The pyridazinone compound (I) and pharmacologically acceptable salt thereof in the present invention promote angiogenesis and potentiate the angiogenic effect of a drug having such effect, and are useful as an angiogenesis promoter and potentiator. Therefore, they are effective for the promotion of healing of various diseases wherein angiogenesis plays an important role, such as promotion of wound healing, promotion of adhesion after skin implantation, promotion of healing after re-suture on quadruple amputation, trichogenous promotion and the like.

This application is based on a patent application No. 232644/1997 filed in Japan, the contents of which are hereby incorporated by reference.

What is claimed is:

1. A method of promoting angiogenesis, which comprises administering a pyridazinone compound of the formula (I)

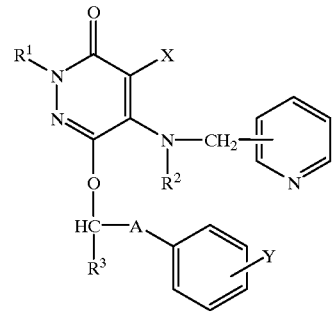

(I)

wherein $R^1$, $R^2$ and $R^3$ are each independently a hydrogen atom or a lower alkyl, X is a halogen atom, cyano or a hydrogen atom, Y is a halogen atom, trifluoromethyl or a hydrogen atom, and A is $C_1$–$C_8$ alkylene optionally substituted by hydroxyl group, or a pharmacologically acceptable salt thereof.

2. The method of claim 1, wherein the pyridazinone compound is a compound of the formula (I) wherein $R^1$ and $R^2$ are each a hydrogen atom, $R^3$ is a hydrogen atom or alkyl having 1 to 4 carbon atoms, X is a halogen atom, Y is a halogen atom or a hydrogen atom, and A is $C_1$–$C_5$ alkylene optionally substituted by hydroxyl group.

3. The method of claim 1, wherein the pyridazinone compound of the formula (I) is 4-bromo-6-[3-(4-chlorophenyl)-propoxy]-5-(3-pyridylmethylamino)-3(2H)-pyridazinone.

4. A method of potentiating an angiogenic effect of a drug having such effect, which comprises administering a pyridazinone compound of the formula (I)

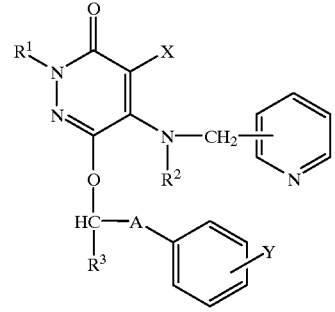

(I)

wherein $R^1$, $R^2$ and $R^3$ are each independently a hydrogen atom or a lower alkyl, X is a halogen atom, cyano or a hydrogen atom, Y is a halogen atom, trifluoromethyl or a hydrogen atom, and A is $C_1$–$C_8$ alkylene optionally substituted by hydroxyl group, or a pharmacologically acceptable salt thereof.

5. The method of claim 4, wherein the pyridazinone compound is a compound of the formula (I) wherein $R^1$ and $R^2$ are each a hydrogen atom, $R^3$ is a hydrogen atom or alkyl having 1 to 4 carbon atoms, X is a halogen atom, Y is a halogen atom or a hydrogen atom, and A is $C_1$–$C_5$ alkylene optionally substituted by hydroxyl group.

6. The method of claim 4, wherein the pyridazinone compound of the formula (I) is 4-bromo-6-[3-(4-chlorophenyl)-propoxy]-5-(3-pyridylmethylainino)-3(2H)-pyridazinone.

7. The method of claim 4, wherein the drug having the angiogenic effect is a growth factor.

8. The method of claim 7, wherein the growth factor is a basic fibroblast growth factor.

* * * * *